United States Patent [19]

Vogel

[11] Patent Number: 5,169,391
[45] Date of Patent: Dec. 8, 1992

[54] CANNULA, IN PARTICULAR FOR PUNCTURING BLOOD VESSELS

[75] Inventor: Dieter Vogel, Steinau, Fed. Rep. of Germany

[73] Assignee: Suddeutsche Feinmechanik GmbH, Fed. Rep. of Germany

[21] Appl. No.: 659,368

[22] PCT Filed: Sep. 22, 1989

[86] PCT No.: PCT/EP89/01102
§ 371 Date: Mar. 15, 1991
§ 102(e) Date: Mar. 15, 1991

[87] PCT Pub. No.: WO90/03195
PCT Pub. Date: Apr. 5, 1990

[30] Foreign Application Priority Data

Sep. 24, 1988 [DE] Fed. Rep. of Germany ... 8812099[U]

[51] Int. Cl.$^5$ .............................................. A61M 5/32
[52] U.S. Cl. ................................. 604/177; 604/198; 604/263; 604/272
[58] Field of Search ............... 604/161, 162, 164, 165, 604/171, 174, 177, 198, 263, 272, 280, 158, 159, 192

[56] References Cited

U.S. PATENT DOCUMENTS

| 3,910,272 | 10/1975 | Forberg ................ 604/161 |
| 4,445,893 | 5/1984 | Bodicky ................ 604/165 |
| 4,563,177 | 1/1986 | Kamen ................ 604/177 |
| 4,676,783 | 6/1987 | Jagger et al. ........ 604/171 |
| 4,781,692 | 11/1988 | Jagger et al. ........ 604/164 |
| 4,950,242 | 8/1990 | Alvarez ................ 604/110 |

Primary Examiner—C. Fred Rosenbaum
Assistant Examiner—C. Maglione
Attorney, Agent, or Firm—Bierman and Muserlian

[57] ABSTRACT

A cannula for puncturing blood vessels comprising a beveled cannula tip and a cannula holder wherein the cannula is fixedly mounted, the cannula holder having at its rear end a flexible tube and being at least partially surrounded by a wing-shaped handle and a protector cap covering the cannula tip, wherein the protector cap and the handle are formed as a unit, which is slipped onto the said holder from the cannula tip, the said cannula holder comprises a locking collar and the said handle comprises a snap-in groove whereby said locking collar is locked in said snap-in groove when the unit is mounted on the cannula holder and the said cannula holder is provided with a shoulder facing said tube at a distance from said handle.

7 Claims, 5 Drawing Sheets (X)

CANNULA, IN PARTICULAR FOR PUNCTURING BLOOD VESSELS

The present invention relates to a cannula, in particular for puncturing blood vessels, for example for extracorporeal blood therapy, comprising a beveled cannula tip and a cannula holder in which the cannula is mounted, which cannula holder carries on its rear end a flexible tube and is surrounded, at least by sections, by a wing-shaped handle, and comprising further a protector cap covering the cannula tip.

Cannulas of this type are employed, for example, for puncturing body cavities and blood vessels, for example for the purpose of withdrawing blood or for introducing blood or other liquids. It is frequently necessary in such applications that the cannula must dwell in the vessel for an extended period of time, for example for blood dialysis. It must be ensured in these cases that the opening of the cannula cannot be blocked by the wall of the vessel. In order to eliminate this risk, and to provide optimum flow conditions, the cannula is designed in such a way that it can be rotated relative to the handle, which latter may have the shape of a wing and be taped in place on the patient's skin. Given the fact that the flexible tube is normally in contact with the handle, more or less, different torques are typically encountered when rotating the cannula so that exact positioning of the needle is often difficult, and there is always the risk that the blood vessels may be injured.

Now, it is one of the objects of the present invention to improve a cannula of the type described above in such a way that equal conditions are always encountered when turning the cannula so that it is ensured at all times that the opening of the cannula can be turned in the blood vessel safely and without any problems. Further, it is an object of the present invention to give the handle a clearly defined position on the cannula holder. In addition, the invention is to ensure that the handle occupies a desired radial position relative to the cannula holder Finally, the invention is to provide means to enable a used needle to be safely put back into the protector cap.

The invention achieves these objects substantially by the fact that a flexible tube is arranged on the cannula holder at a defined distance from the handle. Preferably, the cannula holder is provided with a shoulder, which may run all around its circumference and with which the flexible tube is pushed into contact. Consequently, the arrangement according to the invention guarantees that the flexible tube is kept clear of the handle so that, consequently, it cannot exercise an uncontrolled influence on the torque when the cannula is turned. As a result of this arrangement, the torques encountered are clearly defined which ensures safe handling of the cannula.

According to one embodiment of the invention, the cannula holder is equipped with a flange which is provided at a certain distance from the rear end of the cannula holder and which is contacted by the flexible tube. If desired, a cylindrical portion of the handle surrounding the cannula holder may also rest against the flange on its opposite side. In addition, there are of course other possibilities of maintaining a spacing between the flexible tube and the handle.

In order to fix the cannula in defined positions, for example in a blood vessel, it is proposed according to an independent aspect of the invention to arrange the handle on the cannula holder in such a way that it can be locked in position. To this end, the cannula holder and/or the handle may be provided with interacting detent projections and detent recesses. The arrangement may be such that the handle rests against a stop projecting from the cannula holder, preferably in the area facing the cannula tip, and that detent pins and/or snap-in recesses extending from the stop, in axial direction of the cannula holder, are provided to interact with detent recesses and/or detent lugs extending from the end portion of the handle which surrounds the cannula holder.

In order to fix the handle in place on the cannula holder, in axial direction, a groove is provided, preferably in the handle, for receiving at least sections of a locking collar projecting from the cannula holder. There is of course also the possibility to provide a locking collar on the handle and a detent recess on the cannula holder. And there is also the possibility to combine these two solutions.

Any unwanted rotation of the handle relative to the cannula holder may be prevented by providing a projection extending in the axial direction and, at least by sections, within an axial recess provided in the cylindrical portion of the handle. It is ensured in this manner, by sort of a groove-and-tongue joint, that the handle cannot turn relative to the cannula holder and, thus, to the needle as such.

The proposals set forth above permit the handle to be fixed on the cannula holder in both the axial and the radial sense.

According to another aspect of the invention, the protector cap and the handle are formed integrally with the predetermined breaking point. This provides a particularly contamination-tight closure.

In order to enable the needle to be put back safely into the protector cap, the following features are proposed to be used individually or in combination.

According to an independent aspect of the invention, the protector cap may comprise a tubular insertion piece in its forward end portion, and a pierceable diaphragm may be provided at a certain distance from the end face. The design of the insertion piece may be funnel-like, proceeding from the end face.

With respect to the diaphragm, this arrangement provides the advantage that when the cannula pierces the diaphragm, it gains a safe hold so that it can no longer get detached in an uncontrolled way. This leads to improved safety for the user and excludes any injuries by the cannula tip.

Other possibilities of accommodating the used needle in the protector cap consist in providing at least one pocket extending in longitudinal direction along the outer wall of the protector cap, for receiving a needle which preferably can be guided into the pocket via a channel-like recess disposed in the outer wall of the protector cap, outside the pocket.

In addition, the cannula holder may comprise a portion extending on its outside, towards the cannula tip, along which the rear end of the protector cap can slide so as to hold the cap in place and secure it against uncontrolled removal.

Other details, advantages and features of the invention will become obvious not only from the claims, the features set forth in the latter, taken each individually and/or in combination, but also from the preferred embodiments shown in the drawing which illustrate the essential features of the invention.

Figure 1:
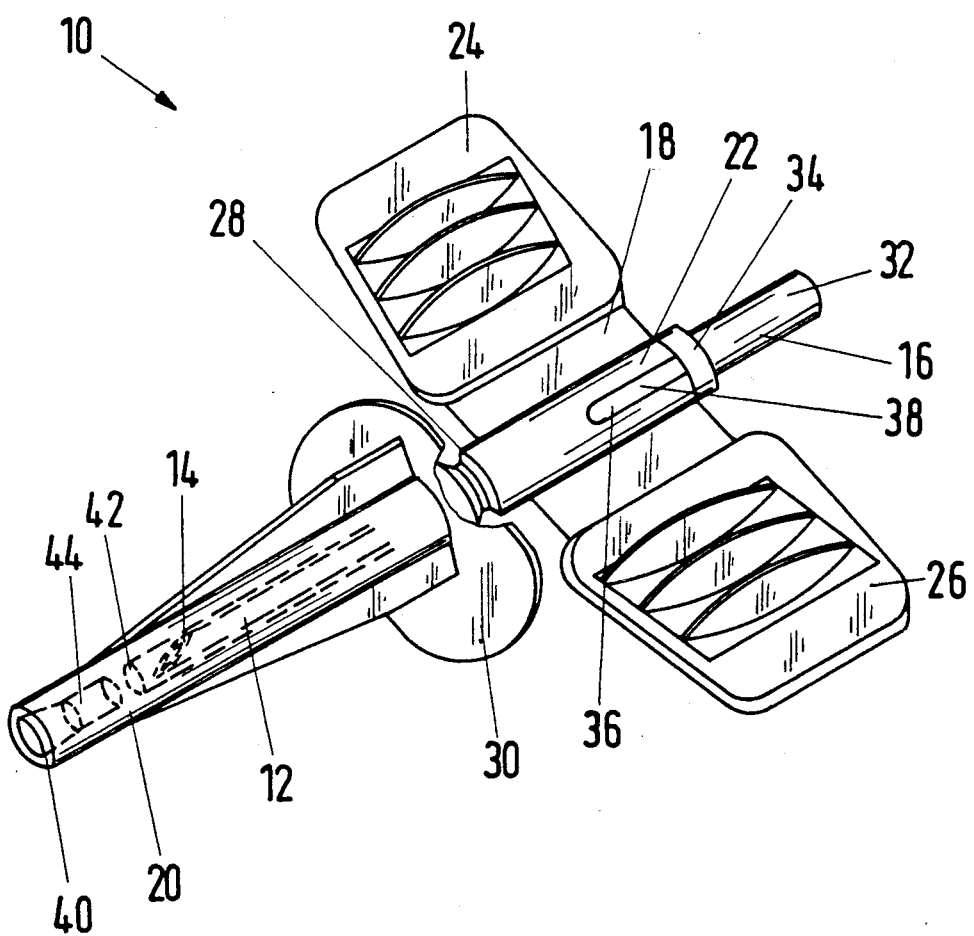
FIG. 1 shows a perspective representation of a cannula.

The representations of the figures, where identical elements are identified by the same reference numerals, illustrate different embodiments of cannulas which are intended, in particular, for puncturing blood vessels, for example for the purpose of extracorporeal blood therapy. The illustrated cannulas are composed substantially of a cannula or needle (12) with beveled tip (14), a cannula holder (16) surrounding the rear portion of the cannula, a preferably wing-shaped handle (18) and a protector cap (20). The cannula holder (16) may be integrally molded with the cannula (12) or fixed thereon by gluing, shrinking or by similar means so as to be securely fixed in position. The handle (18) comprises preferably two wings (24) and (26), which extend from a cylindrical portion (22) surrounding the cannula holder (16) and which, after puncturing of a blood vessel, are taped in place on the skin in order to fix the handle against displacement.

The protector cap (20) is joined to the handle (18), preferably via a predetermined breaking point. In the area of this predetermined breaking point, the protector cap (28) is equipped with an impact guard which may have the form of a flange-line extension (30) extending perpendicularly to the longitudinal axis of the protector cap (20).

A flexible tube—not shown in the drawing—is pushed over the rear portion (32) of the cannula holder (16). In order to exclude any uncontrolled influence of the flexible tube on the turning movements of the handle (18), which might result in varying torques that may in turn impair the handling characteristics of the unit, it is provided according to the invention that the flexible tube is seated on the portion (32) at a defined distance from the handle (18). There is provided to this end a shoulder (34) which serves as abutment for the end face of the flexible tube. The shoulder (34) may be designed in the manner of a flange so that the handle (18), too, may come to rest against the shoulder (34), at its face opposite the flexible tube. In order to fix the handle (18) against rotation, relative to the cannula holder (16) and, thus, the cannula (12), locking means are provided, for example in the form of a groove-and-tongue connection. In the embodiment of the cannula (10) illustrated in FIG. 1, this connection is achieved by a linear projection (38) extending along the cannula holder (16) in the direction of the cylindrical portion (22) of the handle (18), which projection (38) engages a matching recess (36) in the handle (18), whereby any radial rotary movement is excluded.

The protector cap (20) comprises, at a certain distance from its end portion (40), a diaphragm (42) which guarantees sufficient sterility of the cannula when out of use, i.e. which provides the necessary protection for the cannula. The diaphragm (42) and the end portion (40) define between them a funnel-shaped insertion piece (44) into which a used cannula can be introduced, which then pierces the diaphragm (42). A suitable design ensures that a used cannula will be safely received in the protector cap (20). Other solutions for accommodating the needle will be discussed further below, in connection with FIG. 11.

Figure 2:
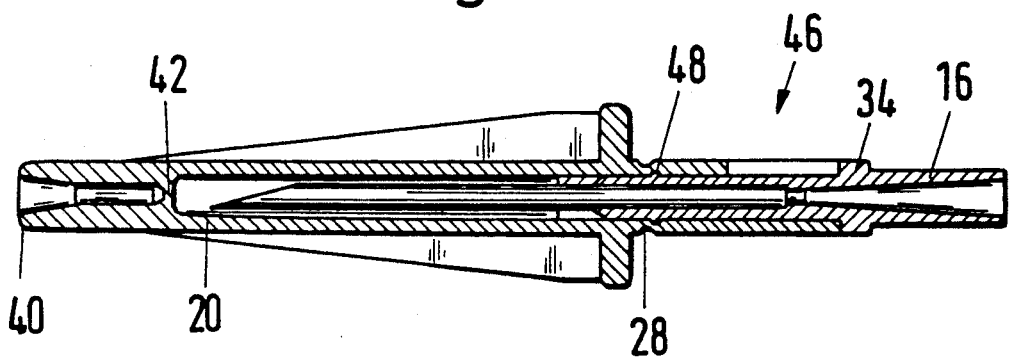
FIG. 2 shows a section through a cannula.
Figure 3:
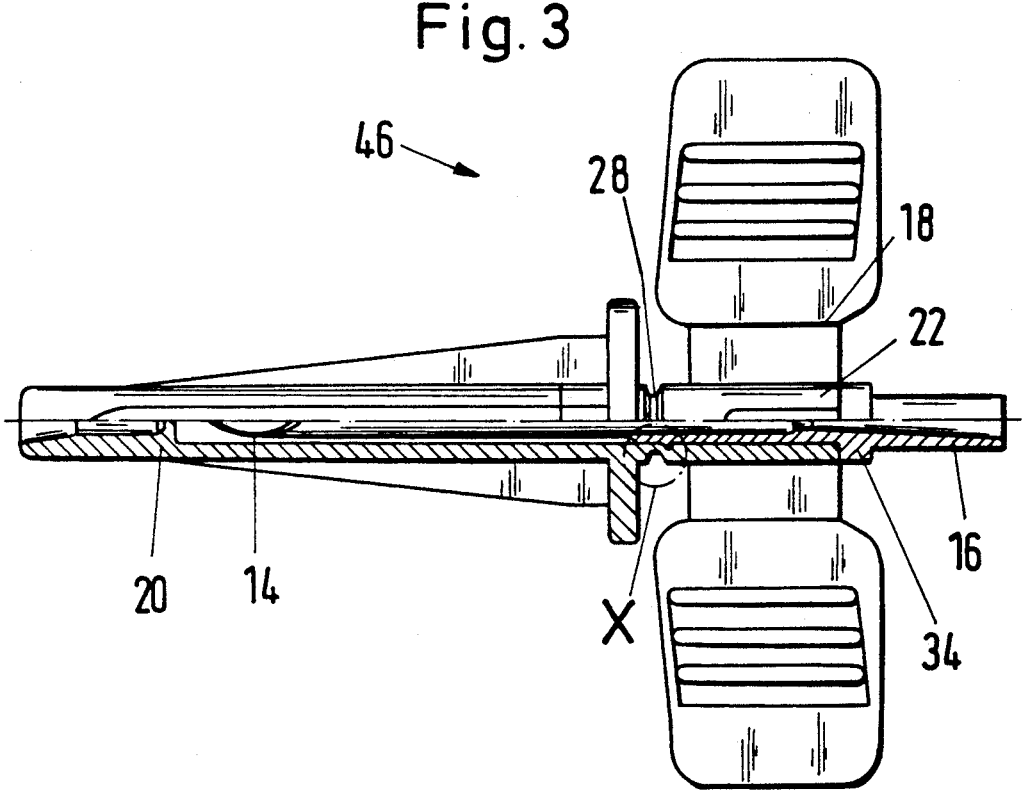
FIG. 3 shows a section through the cannula according to FIG. 2, but turned by 90°.
Figure 4:
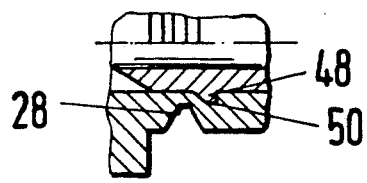
FIG. 4 shows a detail of the cannulas of FIGS. 2 and 3.

FIGS. 2 to 4 show a cannula (46), generally similar to that of FIG. 1, where the handle (18) is fixed against axial displacement relative to the cannula holder (16). The cannula holder (16) comprises a locking collar (48) extending all around its circumference and coacting with a locking groove (50) provided in the inner wall of the cylindrical portion (22) of the handle (18). On assembly of the cannula, therefore, it is only necessary to slide the handle, with the protector cap (20) which preferably may be formed integrally with the handle, onto the cannula holder (16), from the side of the cannula tips (14), until the collar (48) and the groove (50) engage each other so as to lock the parts in position. Additional security from rotary movements may be provided by the groove (36) and the projection (38) on the handle (18) and the cannula holder (16), as illustrated in FIG. 1.

FIGS. 2 to 4 further show with great clarity the predetermined breaking point (28) which serves to remove the protector cap (20) quickly and safely when the cannula is to be used. In addition, one can also see the diaphragm (42) which extends at a distance from the end portion (40) and which has a thickness of, preferably, less than 1 mm.

Figure 5:
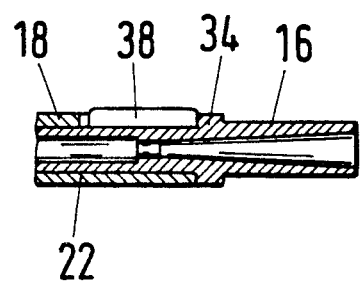
FIG. 5 shows a detail of another embodiment of a cannula.
Figure 6:
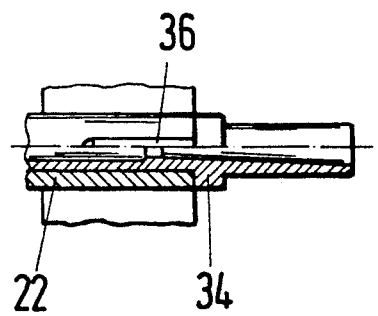
FIG. 6 shows, by comparison with the representation of FIG. 5, a detail of the cannula turned by 90°.

FIGS. 5 and 6 show details of the cannula, in the area of the connection between the cannula holder (16) and the handle (18). One clearly sees the shoulder (34) extending all around the circumference, whose outer surface, i.e. whose right side as viewed in the drawing, serves as stop surface for a flexible tube which is not shown in the drawing, while its inner surface, i.e. the left surface, serves as abutment for the end face of the cylindrical portion (22). Further, the portion (22) comprises the longitudinal groove (36) which is engaged by the projection (38) for securing the handle (18) against rotation.

Figure 7:
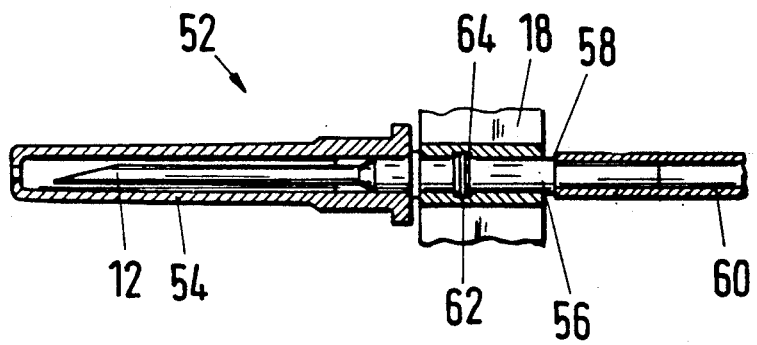
FIG. 7 shows a sectional view of an embodiment of a cannula with protector cap.

FIG. 7 illustrates a detail of a cannula (52) where a handle (54) is designed as an element separate from the cap (18). Instead of the disk-like projection (34) extending all around the circumference and serving as a double-sided stop for the flexible tube on the one hand and the handle on the other hand, as illustrated in FIGS. 1 to 6, the cannula holder (56) illustrated in this figure is provided with a shoulder (58) serving as an abutment for the flexible tube (60). The handle (18) is connected with the cannula holder (56) by means of a locking collar (62) which engages an associated all-around groove (64) when the handle (18) is pushed fully down.

Figure 8:
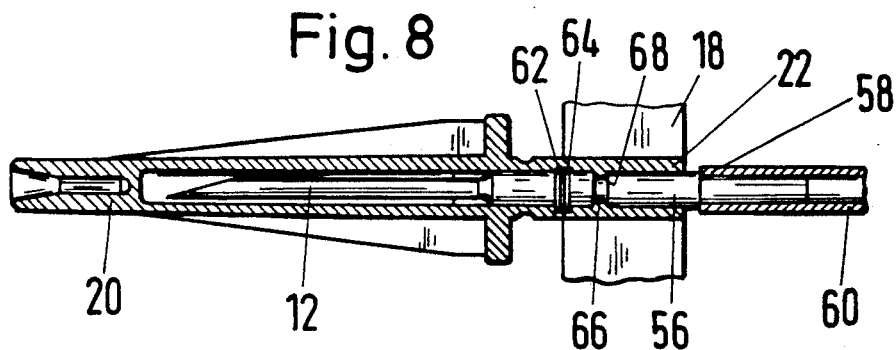
FIG. 8 shows a preferred embodiment of a cannula with protector cap.

In addition to the locking collar (62) and the locking groove (64), the embodiment illustrated in FIG. 8 is provided with a projection (66) extending all around the inner surface of the cylindrical portion (22) of the handle (18) and engaging a groove (68) in the cannula holder (56). This provides sort of a double locking mechanism between the cannula holder (56) and the handle (18). The connection between the handle (18) and the protector cap (20), as well as the latter's design, are identical to FIG. 1.

Figure 9:
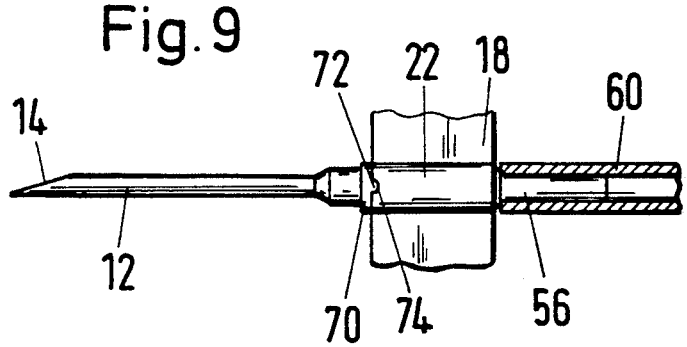
FIGS. 9 and 10 show further details of embodiments of a cannula.

FIG. 9 illustrates one possible design of a lockable rotary connection between the handle (18) and the cannula holder (56), by means of which the handle (18) can be fixed in desired positions relative to the cannula holder. The cannula holder (56) is provided for this purpose with a collar-shaped projection (70) extending all around its circumference. Lugs (72) extending from the projection (70) is axial sense and in the direction of the handle engage in matching locking grooves (74) in the cylindrical portion (22) of the handle (18).

Figure 10:
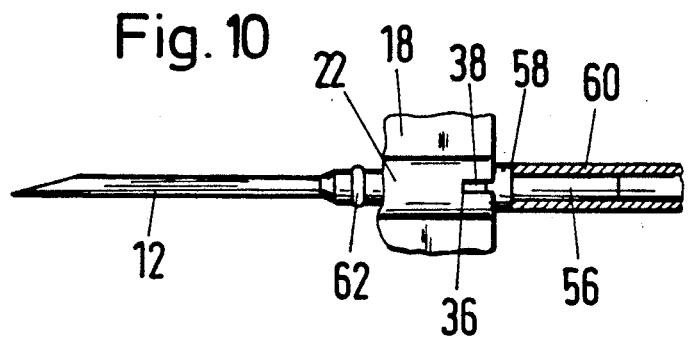

According to FIG. 10, the cylindrical portion (22) and, thus, the handle (18) are interconnected on the one hand by the locking collar (62) and, on the other hand, by the projection (38) and the groove (36). The locking collar, therefore, excludes any sliding movement in the axial direction. The interaction between the groove (36) in the cylindrical portion (22) and the projection (28) extending from the cannula holder (56) in axial direction excludes any rotary movement.

Figure 11:
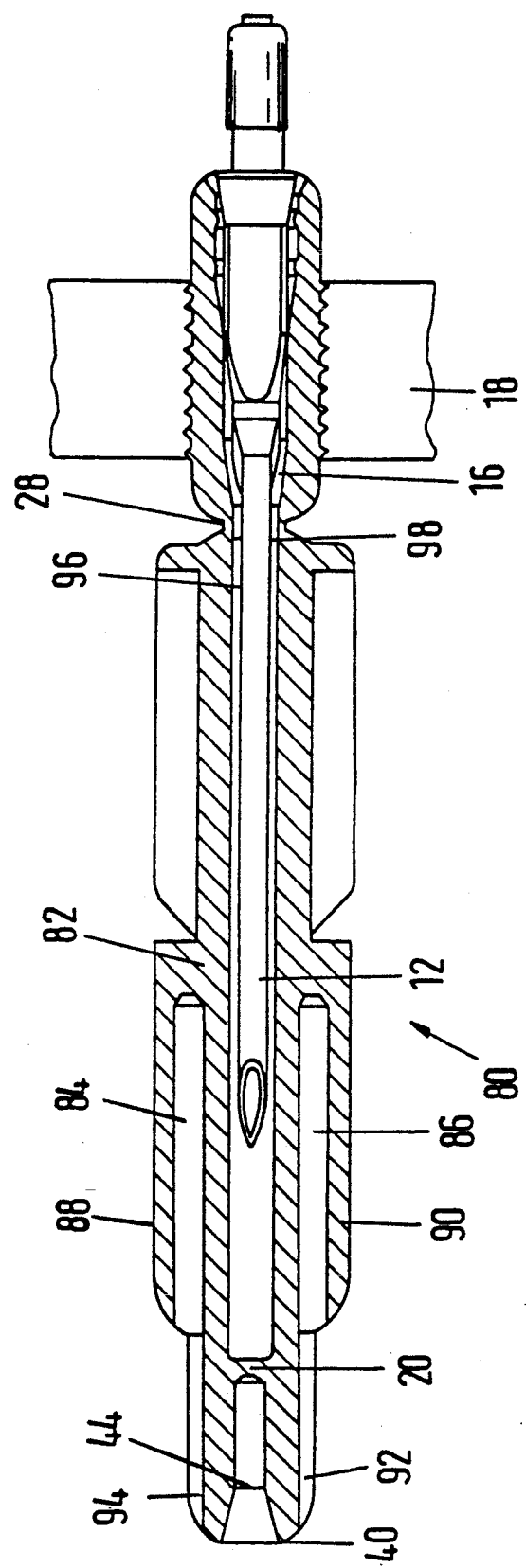
FIG. 11 shows another embodiment of a cannula according to the invention.

FIG. 11 shows another embodiment of a cannula (18) according to the invention comprising a protector cap (82) which offers additional possibilities of returning the needle (12) to within the protector cap. One possibility consists in the diaphragm (20), which has already been described in connection with FIGS. 1, 2 and 3, and which extends at a distance from the end face (40) of the protector cap (82). The diaphragm (20) and the end face (40) define between them a funnel-shaped opening (44) which facilitates the process of introducing the needle (12).

Another possibility of securing a used needle to the protector cap (82) is provided by the cylindrical recesses (84) and (86) extending in the longitudinal direction of the protector cap (82). The cylindrical recesses (84) and (86) are adapted to the diameter of the needle (12) and extend into protrusions (88) and (90) projecting from the outside of the protector cap (82). The protrusions (88) and (90) form together with the recesses (84) and (86) sort of pockets for the used needles (12) to be accommodated. In order to facilitate the introduction into the recesses (84) and (86), groove-like recesses (92) and (94) are provided in the outer wall of the protector cap (82), commencing preferably in the end portion (40) and terminating in the recesses (84) and (86). It is obvious that this arrangement facilitates the introduction of the used needles (12) into the pockets (84) and (86).

Another possibility of returning a used needle (12) to a position inside the protector cap is obtained when the end face (96) of the cannula holder (16) is positioned in front of the predetermined breaking point (28) between the cannula cap (82) and the handle (18) so that the protector cap can be restored to its position on the needle (12) and on the shoulder (98) of the cannula holder (16) which surrounds the needle (12) outside the handle (18).

Preferably, the diaphragm (20), the receiving pockets (84) and (86), and the receiving portion (98) are implemented in a cannula according to the invention in order to provide different possibilities of keeping a used needle (12) safely inside the cannula holder.

I claim:

1. A cannula for puncturing blood vessels comprising a beveled cannula tip and a cannula holder wherein the cannula is fixedly mounted, the cannula holder having at its rear end a flexible tube and being at least partially surrounded by a wing-shaped handle and a protector cap covering the cannula tip, wherein the protector cap and the handle are formed as a unit, which is slipped onto the said holder from the cannula tip, the said cannula holder comprises a locking collar and the said handle comprises a snap-in-groove whereby said locking collar is locked in said snap-in groove when the unit is mounted on the cannula holder, the said cannula holder is provided with a shoulder facing said tube at a distance from said handle the said protector cap being provided on its outer wall with at least one axially extending, hollow cylindrical pocket for receiving the used cannula.

2. Cannula according at least to claim 1, wherein the said handle (18) is in contact with a stop (70) which extends from the cannula holder (56), preferably in the area facing the cannula tip (40), and that detent pins (72) or snap-in recesses extend from the said stop, in an axial direction of the said cannula holder (56), and are provided to interact with detent recesses (74) or detent lugs which extend from an end portion (22) of the said handle (18) which surrounds the said cannula holder (56).

3. Cannula according at least to claim 1, wherein any unwanted rotation of the said handle (18) relative to the said cannula holder (16) is prevented by a conveniently adapted projection (38) which extends from the said cannula holder (16) and engages a linear axial recess formed in the said handle (18).

4. Cannula according to claim 1, wherein at least one channel-like recess (92, 94) extends from an end face (40) of the said protector cap (82) and terminates in the said pocket (84, 86).

5. Cannula according to claim 1, wherein the said cannula holder (16) comprises a portion (98) extending towards the cannula tip which, regarded from the side of the cannula tip, is located in front of a predetermined breaking point found (28) in the said handle (18).

6. Cannula according to claim 1 wherein the said cannula holder (16) is equipped with a flange (34) which is provided at a certain distance from the rear end of the cannula holder and which is contacted by the flexible tube.

7. Cannula according to claim 6 wherein a portion (22) of the said handle (18) surrounding the said cannula holder (16) rests against the said flange (34) on a face opposite the flexible tube.

* * * * *